United States Patent [19]

Martin et al.

[11] 3,980,799

[45] Sept. 14, 1976

[54] USE OF OXIME-ETHERS AS A SYNERGISTICALLY ACTING ADDITIVE TO INSECTICIDALLY AND/OR ACARICIDALLY ACTIVE SUBSTANCES

[75] Inventors: Henry Martin, Basel, Switzerland; Georg Pissiotas, Loerrach, Germany; Volker Dittrich, Basel, Switzerland

[73] Assignee: Ciba-Geigy AG, Basel, Switzerland

[22] Filed: Apr. 1, 1970

[21] Appl. No.: 24,890

[30] Foreign Application Priority Data

Apr. 14, 1969 Switzerland.................... 5613/69

[52] U.S. Cl.............................. 424/278; 424/327
[51] Int. Cl.$^2$................ A01N 9/20; A01N 9/28
[58] Field of Search............... 424/327, 278; 260/566 AE

[56] References Cited

UNITED STATES PATENTS

| | | | |
|---|---|---|---|
| 2,712,031 | 6/1955 | Huffman | 260/562 |
| 3,236,889 | 2/1966 | Pawloski | 260/566 |

OTHER PUBLICATIONS

Nihles, Chem. Abst. vol. 71, 90213Q 1969.
Wolfenbarger et al., Chem. Abst. vol. 68, 104126r, 1968.

Primary Examiner—James O. Thomas, Jr.
Assistant Examiner—Allen J. Robinson
Attorney, Agent, or Firm—Frederick H. Rabin; Harry Goldsmith

[57] ABSTRACT

The present invention is based on the observation that certain oxime-ethers show a synergistic effect when used with insecticidally and/or acaricidally active substances.

1 Claim, No Drawings

USE OF OXIME-ETHERS AS A SYNERGISTICALLY ACTING ADDITIVE TO INSECTICIDALLY AND/OR ACARICIDALLY ACTIVE SUBSTANCES

The present invention relates to insecticidal and/or acaricidal composition comprising an oxime-ether together with an insecticidally and/or acaricidally active substance.

The present invention is based on the observation that the oxime-ethers of the formula (I) given below show a synergistic effect when used with insecticidally and/or acaricidally active substances.

The present invention thus provides an insecticidal and/or acaricidal preparation comprising an oxime-ether of the general formula

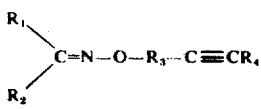
(I)

wherein $R_1$ represents an unsubstituted or substituted aromatic radical, $R_2$ represents a hydrogen atom, a nitrile group or a $C_1$–$C_4$ alkyl radical, $R_3$ represents a straightchain alkylene radical and $R_4$ represents a hydrogen or halogen atom and an insecticidally and/or acaricidally active substance, optionally together with a carrier and/or other additive.

A possible aromatic radical for $R_1$ is preferably the phenyl or naphthyl ring.

The substituents on the aromatic radicals can be of first order or of second order. By substituents of first order, electron donors which intensify the basicity are to be understood. As electron donors, there may be mentioned, for example, the following: halogen atoms, for example, fluorine, chlorine, bromine or iodine atoms, alkyl, alkenyl, alkinyl, mono- and di-halogenalkyl, alkoxy, alkenoxy, alkinoxy, alkoxyalkenyl and alkylthio groups which are branched or unbranched and possess 1 to 4 carbon atoms, preferably 1 to 2 carbon atoms, a methylene-dioxide group, a primary, secondary and especially tertiary amino group, wherein alkyl and alkanol groups are preferred substituents, hydroxyl and mercapto groups.

Acidifying electron acceptors are to be understood as second order substituents. As such substituents, there may be mentioned, for example, the following: nitroso, nitro and nitrile groups, trihalogenalkyl groups, wherein halogen preferably represents fluorine and/or chlorine, lower alkylsulphinyl and lower alkylsulphonyl groups, of which the alkyl radical is branched or unbranched and possesses 1 to 4, preferably 1 to 2, carbon atoms. The $C_1$ to $C_4$ alkyl radicals which $R_2$ represents can be branched or straight-chain, substituted or unsubstituted. Possible substituents are, for example, halogen atoms, for example, fluorine, chlorine, bromine or iodine atoms, and NC- and $O_2N$- groups. Such alkyl groups are for example: methyl, ethyl, trifluoromethyl, propyl, isopropyl, n-, i-, sec.- and tert.butyl. The straight-chain alkyl radicals which are possible for $R_3$ possess 1 to 4 carbon atoms and can be unsubstituted or substituted.

Possible substituents are, amongst others, the same groups as in the case of the $C_1$–$C_4$ alkyl radicals which $R_2$ represents. In the case of $R_4$, fluorine, chlorine, bromine and/or iodine are possible halogen atoms.

The following compounds are, for example, insecticidally and/or acaricidally active substances:

Phosphoric acid derivatives

Bis-o,o-diethylphosphoric acid anhydride (TEPP), O,O,O,O-tetrapropyldithiopyrophosphate, dimethyl(2,2,2-trichloro-1-hydroxyethyl)phosphonate (TRICHRORFON), 1,2-dibromo-2,2-dichlorethyl-dimethylphosphate (NALED), 2,2-dichlorovinyldimethylphosphate (DICHLORFOS), 2-methoxycarbamyl-1-methylvinyldimethylphosphate (MEVINPHOS), dimethyl-1-methyl-2-(methylcarbamoyl)vinylphosphate, cis (MONOCROTOPHOS), 3-(dimethoxyphosphinyloxy)-N-methyl-N-methoxy-cis-crotonamide, 3-(dimethoxyphosphinyloxy)-N,N-dimethyl-cis-crotonamide (DICROTOPHOS), 2-chloro-2-diethylcarbamoyl-1-methylvinyldimethylphosphate (PHOSPHAMIDON), O,O-diethyl-O(or S)-2-(ethylthio)-ethylthiophosphate (DEMETON), S-ethylthioethyl-O,O-dimethyl-dithiophosphate (THIOMETON), O,O-diethyl-S-ethylmercaptomethyldithiophosphate (PHORATE), O,O-diethyl-S-2-[(ethylthio)ethyl]dithiophosphate (DISULFOTON), O,O-dimethyl-S-2-(ethylsulphinyl)ethylthiophosphate (OXYDEMETON-METHYL), O,O-dimethyl-S-(1,2-dicarbethoxyethyl)-dithiophosphate (MALATHION), O,O,O,O-tetraethyl-S,S'-methylene-bis-[dithiophosphate] (ETHION), O-ethyl-S,S-dipropyldithiophosphate, O,O-dimethyl-S-(N-methyl-N-formylcarbamoylmethyl)-dithiophosphate (FORMOTION), O,O-dimethyl-S-(N-methylcarbamoylmethyl)dithiophosphate (DIMETHAT), O,O-dimethyl-S-(N-ethylcarbamoylmethyl)dithiophosphate (ETHOAT-METHYL), O,O-diethyl-S-(N-isopropylcarbamoylmethyl)-dithiophosphate (PROTHOAT), S-N-(1-cyano-1-methylethyl)carbamoylmethyldiethylthiophosphate (CYANTHOAT), S-(2-acetamidoethyl)-O,O-dimethyldithiophosphate, hexamethylphosphoric acid triamide (HEMPA), O,O-dimethyl-O-p-nitrophenylthiophosphate (PARATHIONMETHYL), O,O-diethyl-o-p-nitrophenylthiophosphate (PARATHION), O-ethyl-O-p-nitrophenylphenylthiophosphonate (EPN), O,O-dimethyl-O-(4-nitro-m-tolyl)thiophosphate (FENITROTHION), O,O-dimethyl-O-(2-chloro-4-nitrophenyl)thiophosphate (DICAPTHON), O,O-dimethyl-O-p-cyanophenylthiophosphate (CYANOX), O-ethyl-O-p-cyanophenylphenylthiophosphonate, O,O-diethyl-O-2,4-dichlorophenylthiophosphate (DICHROFENTHION), O-2,4-dichlorophenyl-O-methylisopropylamidothiophosphate, O,O-dimethyl-O-2,4,5-trichlorophenylthiophosphate (RONNEL), O-ethyl-O-2,4,5-trichlorophenylethylthiophosphonate (TRICHLORONAT), O,O-dimethyl-O-2,5-dichloro-4-bromophenylthiophosphate (BROMOPHOS), O,O-diethyl-O-2,5-dichloro-4-bromophenylthiophosphate (BROMOPHO-ETHYL), O,O-dimethyl-O-(2,5-dichloro-4-iodophenyl)-thiophosphate (IODOFENPHOS), 4-tert.butyl-2-chlorophenyl-N-methyl-O-methylamidophosphate (CRUFOMAT), dimethyl-p-(methylthio)phenylphosphate, O,O-dimethyl-O-(3-methyl-4-methylmercaptophenyl)thiophosphate (FENTHION), isopropylamino-O-ethyl-O-(4-methylmercapto-3-methylphenyl)-phosphate, O,O-diethyl-O-p-[(methylsulphinyl) phenyl]-thiophosphate (FENSULFOTHION), O,O-dimethyl-O-p-sulphamidophenylthiophosphate, O-[p-(dimethylsulphamido) phenyl]O,O-dimethylthiophosphate (FAMPHUR), O,O,O',O'-tetramethyl-O,O'-thiodi-p-phenylenethiophosphate, O-(p-(p-chlorophenylazophenyl)O,O-dimethylthiophosphate (AZOTHOAT), O-ethyl-S-phenyl-ethyldithiophosphonate, O-ethyl-S-4-chlorophenyl-ethyldithiophosphonate, O-isobutyl-S-p-chlorophenyl-ethyldithiophosphonate, O,O-dimethyl-S-p-chlorophenylthiophosphate, O,O-dimethyl-S-(p-chlorophenyl-thiomethyl)-dithiophosphate, O,O-diethyl-p-chlorophenylmercaptomethyl-dithiophosphate (CARBOPHENOTHION), O,O-diethyl-S-p-chlorophenylthiomethyl-thiophosphate, O,O-dimethyl-S-(carbethoxyphenylmethyl)dithiophosphate (PHENOTHOAT), O,O-diethyl-S-(carbofluorethoxy-phenylmethyl)-dithiophosphate, O,O-dimethyl-S-(carboisopropoxyphenylmethyl)-dithiophosphate, O,O-dimethyl-O-(alpha-methylbenzyl-3-hydroxycrotonyl)-phosphate, 2-chloro-1-(2,4-dichlorophenyl) vinyl-diethylphosphate (CHLORFENVINPHOS), 2-chloro-1-(2,4,5-trichlorophenyl)vinyl-dimethylphosphate, O-(2-chloro-1-(2,5-dichlorophenyl)vinyl-O,O-diethylthiophosphate, phenylglyoxylonitriloxime-O,O-diethylthiophosphate (PHOXIM), O,O-diethyl-O-(3-chloro-4-methyl-2-oxo-2-H-1-benzopyran-7-yl)-thiophosphate (COUMAPHOS), O,O-diethyl-7-hydroxy-3,4-tetramethylenecoumarinyl-thiophosphate (COUMITHOAT), 2,3-p-dioxanedithiol-S,S-bis(O,O-diethyldithiophosphate) (DIOXANTHION), 2-methoxy-4-H-1,3,2-benzodioxaphosphorine-2-sulphide, O,O-diethyl-O-(5-phenyl-3-isooxyzolyl)thiophosphate, S-[(6-chlor-2-oxo-3-benzoxazolinyl)methyl]O,O-diethyldithiophosphate (PHOSALON), 2-(diethoxyphosphinylimino)-4-methyl-1,3-dithiolane, O,O-dimethyl-S-[2-methoxy-1,3,4-thiadiazol-5-(4H)-onyl-(4)-methyl]dithiophosphate, tris-(2-methyl-1-aziridinyl)-phosphine-oxide (METEPA), O,O-dimethyl-S-phthalimidomethyldithiophosphate, S-(2-chloro-1-phthalimidoethyl)-O,O-diethyldithiophosphate, N-hydroxynaphthalimido-diethylphosphate, dimethyl-3,5,6-trichloro-2-pyridylphosphate, O,O-dimethyl-O-(3,5,6-trichloro-2-pyridyl)thiophosphate, O,O-diethyl-O-(3,5,6-trichloro-2-pyridyl)-thiophosphate, O,O-diethyl-O-2-pyrazinylthiophosphate (THIONAZIN), O,O-diethyl-O-(2-isopropyl-4-methyl-6-pyrimidyl)thiophosphate (DIAZINON), O,O-diethyl-O-(2-quinoxylyl)thiophosphate, O,O-dimethyl-S-(4-oxo-1,2,3-benzotriazin-3 (4H)-ylmethyl)-dithiophosphate (AZINPHOSMETHYL), O,O-diethyl-S-(4-oxo-1,2,3-benzotriazin-3(4H)-ylmethyl)-dithiophosphate (AZINPHOSETHYL), S-[(4,6-diamino-s-triazin-2-yl)methyl]-O,O-dimethyldithiophosphate (MENAZON), S-[2-(ethylsulphonyl)ethyl]-dimethylthiolphosphate (DIOXYDEMETON-S-METHYL), diethyl-S-[2-(ethylsulphinyl)ethyl]dithiophosphate (OXYDISULFOTON), bis-O,O-diethylthiophosphoric acid anhydride (SULFOTEP), dimethyl-1,3-di(carbomethoxy)-1-propen-2-yl-phosphate, dimethyl-(2,2,2-trichloro-1-butyroyloxyethyl)phosphonate BUTONAT), O,O-dimethyl-O-(2,2-dichloro-1-methoxy-vinyl)phosphate, O,O-dimethyl-O-(3-chloro-4-nitrophenyl)thiophosphate (CHLORTHION), O,O-dimethyl-O(or S)-2-(ethylthioethyl)thiophosphate (DEMETON-S-METHYL), bis-(dimethylamido)-fluorophosphate (DIMEFOX), 2-(O,O-dimethyl-phosphoryl-thiomethyl)-5-methoxy-pyrone-4,3,4-dichlorobenzyl-triphenylphosphonium chloride, dimethyl-N-methoxymethylcarbamoylmethyl-dithiophosphate (FORMOCARBAM), O,O-diethyl-O-(2,2-dichloro-1-chlorethoxyvinyl)phosphate, O,O-dimethyl-O-(2,2-dichloro-1-chlorethoxyvinyl)phosphate, O-ethyl-S,S-diphenyldithiolphosphate, O-ethyl-S-benzyl-phenyldithiophosphonate, O,O-diethyl-S-benzyl-thiolphosphate, O,O-dimethyl-S-(4-chlorophenylthiomethyl)dithiophosphate (METHYLCARBOPHENOTHION), O,O-dimethyl-S-(ethylthiomethyl)dithiophosphate, diisopropylaminofluorophosphate (MIPAFOX), O,O-dimethyl-S-(morpholinylcarbamoylmethyl)dithiophosphate (MORPHOTHION), bismethylamido-phenylphosphate, O,O-dimethyl-S-(benzenesulphonyl) dithiophosphate, O,O-dimethyl-(S and O)-ethylsulphinylethylthiophosphate, O,O-diethyl-O-4-nitrophenylphosphate, O,O-diethyl-S-(2,5-dichlorophenylthiomethyl)dithiophosphate (PHENDAPTON), triethoxy-isopropoxy-bis (thiophosphinyl) disulphide, O,O-diethyl-O-(4-methyl-coumarinyl-7)-thiophosphate (POTASAN), 2-methoxy-4H-1,3,2-benzodioxaphosphorine-2-oxide, octamethylpyrophosphoramide (SCHRADAN), bis(dimethoxythiophosphinylsulphido)-phenylmethane, 5-amino-bis(dimethylamido)-phosphinyl-3-phenyl-1,2,4-triazole (TRIAMIPHOS), N-methyl-5-(O,O-dimethylthiolphosphoryl)-3-thiavaleramide (VAMIDOTHION), NNN′N′-tetramethyldiamidofluorophosphate (DIMEFOX).

CARBAMIC ACID DERIVATIVES 1-naphthyl-N-methylcarbamate (CARBARYL), 2-butinyl-4-chlorophenylcarbamate, 4-dimethylamino-3,5-xylyl-N-methylcarbamate, 4-dimethylamino-3,5-tolyl-N-methylcarbamate (AMINOCARB), 4-methylthio-3,5-xylyl-N-methylcarbamate (METHIOCARB), 3,4,5-trimethylphenyl-N-methylcarbamate, 2-chlorophenyl-N-methylcarbamate (CPMC), 5-chloro-6-oxo-2-norbornane-carbonitrile-O-(methylcarbamoyl)-oxime, 1-(dimethylcarbamoyl)-5-methyl-3-pyrazolyl-N,N-dimethyl-carbamate (DIMETILAN), 2,3-dihydro-2,2-dimethyl-7-benzofuranyl-N-methylcarbamate (CARBOFURAN), 2-methyl-2-methylthiopropionaldehyde-O-(methylcarbamoyl)-oxime (ALDICARB), 8-quinaldyl-N-methylcarbamate and its salts, methyl-2-isopropyl-4-(methylcarbamoyloxy)carbanilate, m-(1-ethylpropyl)phenyl-N-methylcarbamate, 3,5-di-tert.butyl-N-methylcarbamate, m-(1-methylbutyl)phenyl-N-methylcarbamate, 2-isopropylphenyl-N-methylcarbamate, 2-sec.butylphenyl-N-methylcarbamate, m-tolyl-N-methylcarbamate, 2,3-xylyl-N-methylcarbamate, 3-isopropylphenyl-N-methylcarbamate, 3-tert.butylphenyl-N-methylcarbamate, 3-sec.butylphenyl-N-methylcarbamate, 3-isopropyl-5-methylphenyl-N-methylcarbamate (PROMECARB), 3,5-diisopropylphenyl-N-methylcarbamate, 2-chlor-5-isopropylphenyl-N-methylcarbamate, 2-chloro-4,5-dimethylphenyl-N-methylcarbamate, 2-(1,3-dioxolan-2-yl)phenyl-N-methylcarbamate (DIOXYCARB), 2-(4,5-dimethyl-1,3-dioxolan-2-yl)phenyl-N-methylcarbamate, 2-(1,3-dioxan-2-yl)phenyl-N-methylcarbamate, 2-(1,3-dithiolan-2-yl)phenyl-N-methylcarbamate, 2-(1,3-dithiolan-2-yl)phenyl-N,N-dimethylcarbamate, 2-isopropoxyphenyl-N-methylcarbamate (ARPROCARB), 2-(2-propinyloxy)phenyl-N-methylcarbamate, 2-(2-propinyloxy)phenyl-N-methylcarbamate, 3-(2-propinyloxy)phenyl-N-methylcarbamate, 2-dimethylaminophenyl-N-methylcarbamate, 2-diallylaminophenyl-N-methylcarbamate, 4-diallylamino-3,5-xylyl-N-methylcarbamate (ALLYXICARB), 4-benzothienyl-N-methylcarbamate, 2,3-dihydro-2-methyl-7-benzofuranyl-N-methylcarbamate, 3-methyl-1-phenylpyrazol-5-yl-N,N-dimethylcarbamate, 1-isopropyl-3-methylpyrazol-5-yl-N,N-dimethylcarbamate (ISOLAN), 2-(N′,N′-dimethylcarbamoyl)-

3-methylpyrazol-5-yl-N,N-dimethylcarbamate, 2-dimethylamino-5,6-dimethylpyrimidin-4-yl-N,N-dimethylcarbamate, 3-methyl-4-dimethylaminomethyleneiminophenyl-N-methylcarbamate, 3-dimethylamino-methyleneiminophenyl-N-methylcarbamate, 1-methylthio-ethylimino-N-methylcarbamate (METHOXYMYL), 2-methylcarbamoyloxyimino-1,3-dithiolane, 5-methyl-2-methylcarbamoyloxyimino-1,3-oxathiolane, 2-(1-methoxy-2-propoxy)phenyl-N-methylcarbamate, 2-(1-butin-3-yl-oxy)phenyl-N-methylcarbamate, 3-methyl-4-(dimethylaminomethyl-mercapto-methyleneimino)phenyl-N-methylcarbamate, 1,3-bis(carbamoylthio)-2-(N,N-dimethylamino)-propane hydrochloride, 5,5-dimethylhydroresorcinol-dimethylcarbamate, 2-[propargylethylamino]-phenyl-N-methylcarbamate, 2-[di-2-[propargylmethylamino]-phenyl-N-methylcarbamate, 2-]dipropargylamino]-phenyl-N-methylcarbamate, 3-methyl-4-[dipropargylamino]-phenyl-N-methylcarbamate, 3,5-dimethyl-4-[dipropargylamino]-phenyl-N-methylcarbamate, 2-[allyl-isopropylamino]-phenyl-N-methylcarbamate, 3-[allyl-isopropylamino]-phenyl-N-methylcarbamate.

Chlorinated hydrocarbons

γ-hexachlorocyclohexane [Gammexane; Lindane; γ HCH], 1,2,4,5,6,7,8,8-octachloro-3α,4,7,7α'-tetrahydo-4,7-methyleneindane [Chlordan], 1,4,5,6,7,8,8-heptachloro-3α,4,7,7α-tetrahydro-4,7-methyleneindane [Heptachlor], 1,2,3,4,10,10-hexachloro-1,4,4α,5,8,8α-hexahydro-endo-1,4-exo-5,8-dimethanonaphthalene [Aldrin], 1,2,3,4,10,10-hexachlor-6,7-epoxy-1,4,4α,5,6,7,8,8α-octahydro-exo-1,4-endo-5,8-dimethanonaphthalene [Dieldrin], 1,2,3,4,10,10-hexachlor-6,7-epoxy-1,4,4α,5,6,7,8,8α-octahydro-1,4endoendo-5,8-dimethanonaphthalene [Endrin], 6,7,8,9,10,10-hexachloro-1,5,5α,6,9,9α-hexahydro-6,9-methano-2,3,4 benzo[e]-dioxa-thiepene-3-oxide [Endosulfan], chlorinated camphor [Toxaphen], decachloroctahydro-1,3,4-metheno-2H-cyclobuta[e d]pentalen-2-one, dodecachloroctahydro-1,3,4-metheno-1H-cyclobuta[c d]pentalene [Mirex], ethyl-1,1α,3,3α,4,5,5α,5,5β,6-decachloroctahydro-2-hydroxy-1,3,4-metheno-1H-cyclobuta[c d]pentalene-2laevulinate, bis(pentachloro-2,4-cyclopentadien-1-yl), dinoctone-o, 1,1,1-trichloro-2,2-bis(p-chlorophenyl)ethane [DDT], dichlorodiphenyl-dichlorethane [TDE], di(p-chlorophenyl)-trichloromethylcarbinol [Dicofol], ethyl-4,4'-dichlorophenylglycollate [Chlorobenzylate], ethyl-4,4'-dibromobenzylate [Bromobenzylate], isopropyl-4,4'-dichlorobenzylate, 1,1,1-trichloro-2,2-bis-(p-methoxyphenyl)ethane [Methoxychlor], diethyl-diphenyldichlorethane, decachloropentacyclo(3,3,2, O$^{2,6}$, O$^{3,9}$, O$^{7,10}$)decan-4-one [Chlordecon].

Nitrophenols and derivatives 4,6-dinitro-6-methylphenol, Na salt [Dinitrocresol], dinitrobutylphenol(2,2',2''-triethanolamine salt), 2-cyclohexyl-4,6-dinitrophenol [Dinex], 2-(1-methylheptyl)-4,6-dinitrophenyl-crotonate [Dinocap], 2-sec.-butyl-4,6-dinitrophenyl-3-methyl-buteneoate [Binapacryl], 2-sec.butyl-4,6-dinitrophenyl-cyclopropionate, 2-sec.butyl-4,6-dinitrophenyl-isopropyl-carbonate [Dinobuton].

Various

Sabadilla, rotenon, cevadin, veratridin, ryania, pyrethrin, 3-allyl-2-methyl-4-oxo-2-cyclopenten-1-yl-chrysanthemumate (Allethrin), 6-chloropiperonyl-chrysanthemumate (barthrin), 2,4-dimethylbenzyl-chrysanthemumate (dimethrin), 2,3,4,5-tetrahydrophthalimidomethylchrysanthemumate, (5-benzyl-3-furyl)-methyl-2,2-dimethyl-3-(2-methylpropanyl)cyclopropanecarboxylate, nicotine, Bacillus thuringiensis Berliner, dicyclohexylcarbodiimide, diphenyldiimide, [Azobenzene], 4-chlorobenzyl-4-chlorophenylsulphide [Chlorbensid], creosote oil, 6-methyl-2-oxo-1,3-dithiolo-[4,5-b]-quinoxaline [Quinomethionate], (I)-3-(2-furfuryl)-2-methyl-4-oxocyclopent-2-enyl(I)-(cis + trans)chrysanthemum-monocarboxylate [Furethrin], 2-pivaloyl-indane-1,3-dione [Pindon], 2-fluorethyl(4-bisphenyl)acetate, 2-fluoro-N-methyl-N(1-naphthyl)-acetamide, pentachlorophenol and salts, 2,2,2-trichloro-N-(pentachlorophenyl)-acetimidoyl chloride, N'-(4-chloro-2-methylphenyl)-N,N-dimethylformamidine (Chlorophenamidine), 4-chlorobenzyl-4-fluorophenyl-sulphide (Fluorobensides), 5,6-dichloro-1-phenoxycarbanyl-2-trifluromethyl-benzimidazole (Fenozaflor), tricyclohexyl-tin hydroxide, 2-thiocyanatoethyl-lauric acid ester, β-butoxy-β'-thiocyanatodiethylether, isobornyl-thiocyanatoacetate, p-chlorophenyl-p-chlorobenzenesulphonate (Ovex), 2,4-dichlorophenyl-benzenesulphonate, p-chlorophenyl-benzenesulphonate (Fenson), p-chlorophenyl-2,4,5-trichlorophenylsulphone (Tetradifon), p-chlorophenyl-2,4,5-trichlorophenylsulphide (Tetrasul), methyl bromide, p-chlorophenyl-phenylsulphone, p-chlorobenzyl-p-chlorophenylsulphide (Chlorbensides), 4-chlorophenyl-2,4,5-trichlorophenylazosulphide, 2-(p-tert.butylphenoxy-1-methylethyl-2-chlorethyl-sulphite, 2-(p-tert.butylphenoxy)cyclohexyl-2-propinyl-sulphite, 4,4'-dichloro-N-methylbenzenesulphonanilide, N-(2-fluoro-1,1,2,2-tetrachlorethylthio)methanesulphonanilide, 2-thio-1,3-dithiolo-(4,5-6)quinoxaline (Thioquinox), chloromethyl-p-chlorophenylsulphone (lauseto new), 1,3,6,8-tetranitrocarbazole, prop-2-ynyl-(4-t-butylphenoxy)-cyclohexylsulphite (Propargil).

The substances defined by the general formula (I) are capable of increasing the activity of such insecticidal and/or acaricidal compounds by a multiple. Surprisingly, it was also found that when using substances of formula (I) insects or representatives of the order Acarina which are resistant towards carbamates or phosphoric acid esters can again be rendered fully sensitive.

Amongst the ethers of formula (I) those of general formula

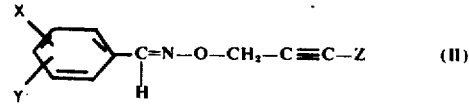

are especially active.

In formula (II) X and Y each represents a hydrogen or chlorine atom or a nitro group, or together represent a methylenedioxy group or a second benzene nucleus fused to the benzene nucleus, and Z represents a hydrogen or iodine atom.

The ethers defined by the general formula (I) in which R$_1$ represents a hydrogen atom are known.

The synthesis of the ethers of formula (I) may be effected in a simple manner by reacting an aldehyde of the formula R$_1$-CHO or a ketone of the formula

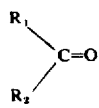

with hydroxylamine and further reacting the resulting oxime with a halide of the formula

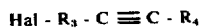

wherein $R_1$ to $R_4$ have the meanings given above for formula (1) and Hal represents chlorine, bromine or iodine atom. This reaction is advantageously carried out in the presence of methanolic sodium methoxide solution.

The following aldehydes or ketones can, for example, be used for the synthesis of ethers of formula (I):

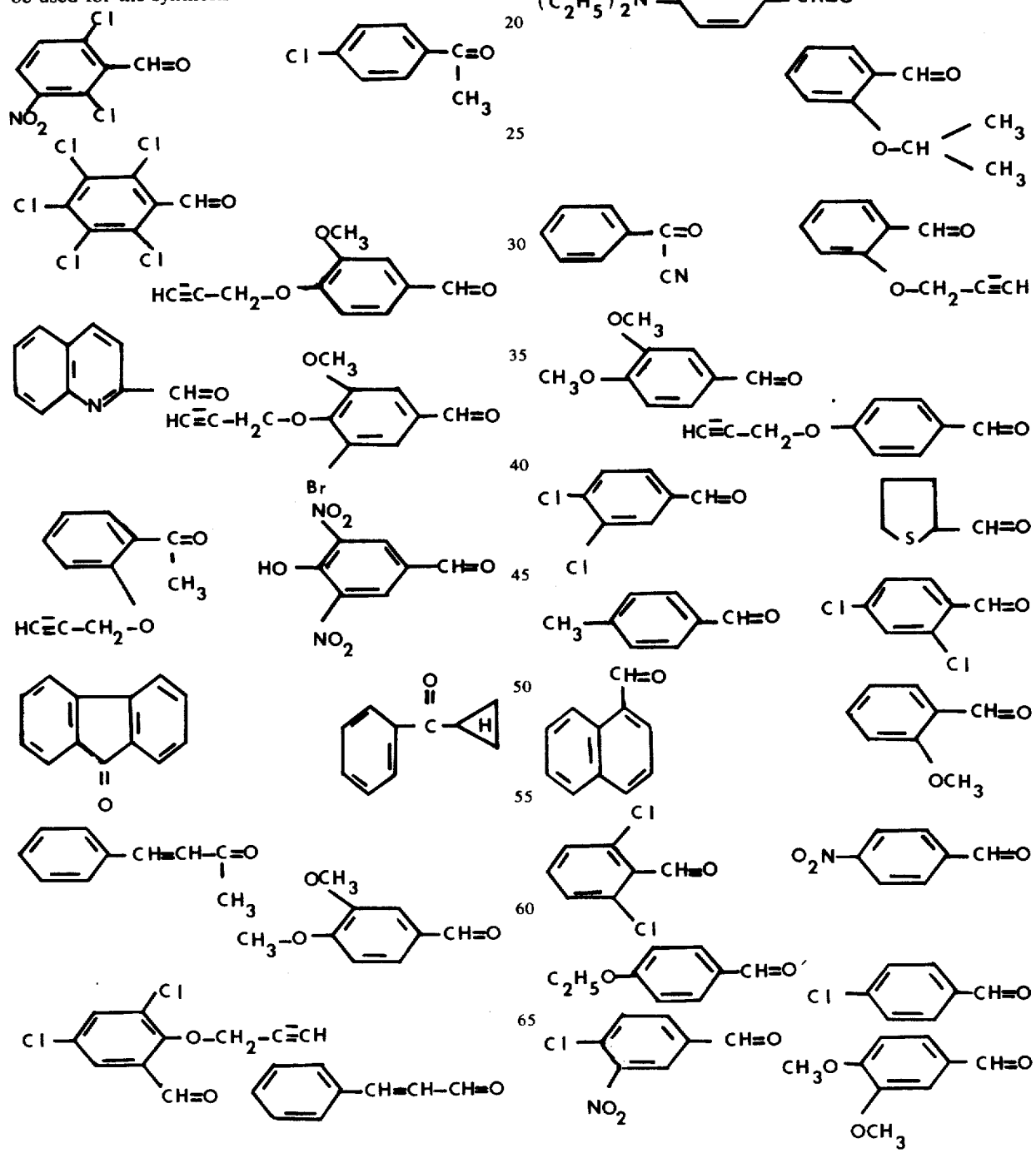

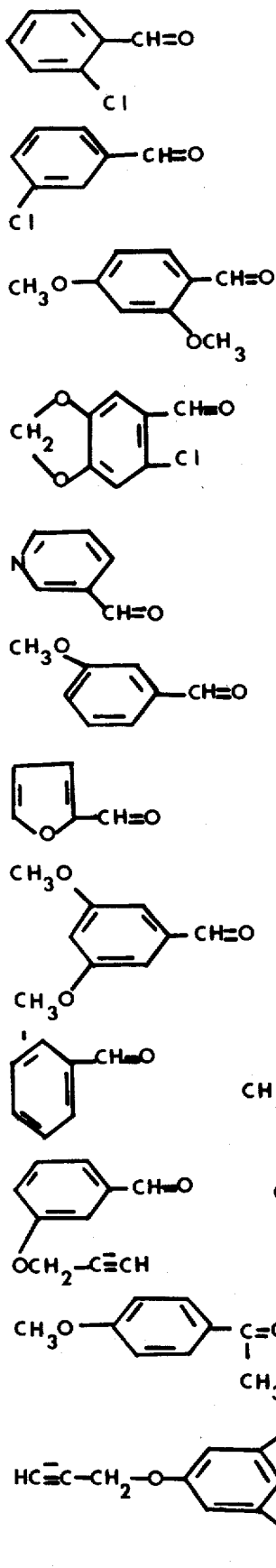
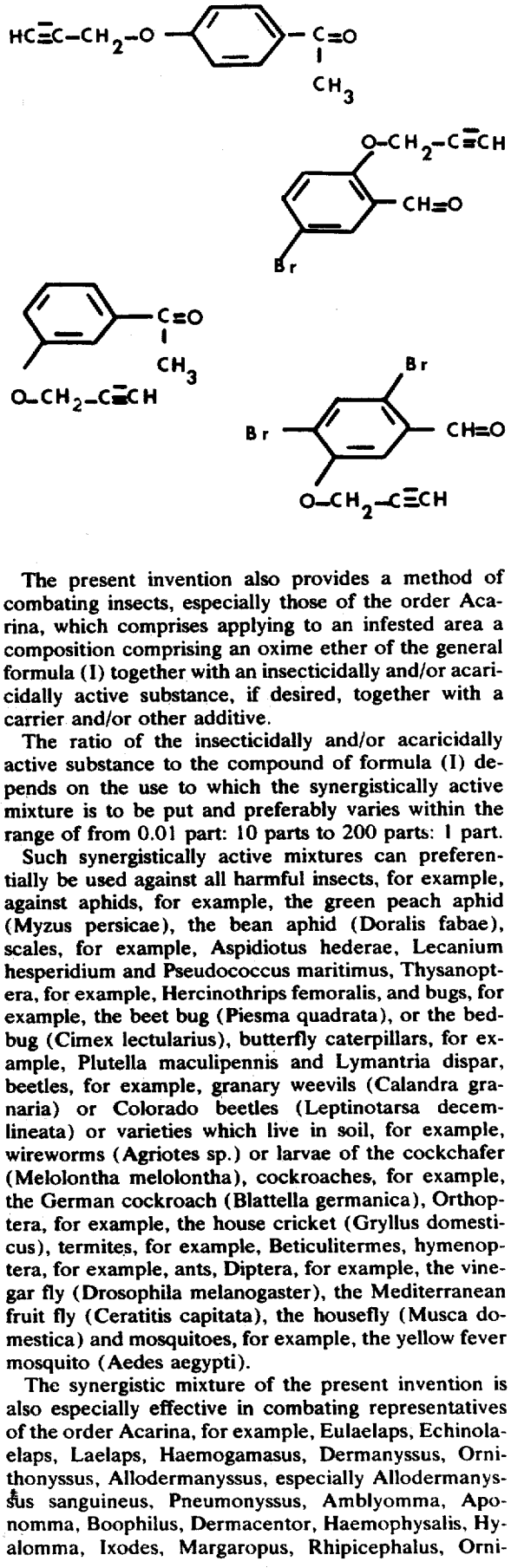

The present invention also provides a method of combating insects, especially those of the order Acarina, which comprises applying to an infested area a composition comprising an oxime ether of the general formula (I) together with an insecticidally and/or acaricidally active substance, if desired, together with a carrier and/or other additive.

The ratio of the insecticidally and/or acaricidally active substance to the compound of formula (I) depends on the use to which the synergistically active mixture is to be put and preferably varies within the range of from 0.01 part: 10 parts to 200 parts: 1 part.

Such synergistically active mixtures can preferentially be used against all harmful insects, for example, against aphids, for example, the green peach aphid (Myzus persicae), the bean aphid (Doralis fabae), scales, for example, Aspidiotus hederae, Lecanium hesperidium and Pseudococcus maritimus, Thysanoptera, for example, Hercinothrips femoralis, and bugs, for example, the beet bug (Piesma quadrata), or the bedbug (Cimex lectularius), butterfly caterpillars, for example, Plutella maculipennis and Lymantria dispar, beetles, for example, granary weevils (Calandra granaria) or Colorado beetles (Leptinotarsa decemlineata) or varieties which live in soil, for example, wireworms (Agriotes sp.) or larvae of the cockchafer (Melolontha melolontha), cockroaches, for example, the German cockroach (Blattella germanica), Orthoptera, for example, the house cricket (Gryllus domesticus), termites, for example, Beticulitermes, hymenoptera, for example, ants, Diptera, for example, the vinegar fly (Drosophila melanogaster), the Mediterranean fruit fly (Ceratitis capitata), the housefly (Musca domestica) and mosquitoes, for example, the yellow fever mosquito (Aedes aegypti).

The synergistic mixture of the present invention is also especially effective in combating representatives of the order Acarina, for example, Eulaelaps, Echinolaelaps, Laelaps, Haemogamasus, Dermanyssus, Ornithonyssus, Allodermanyssus, especially Allodermanyssus sanguineus, Pneumonyssus, Amblyomma, Aponomma, Boophilus, Dermacentor, Haemophysalis, Hyalomma, Ixodes, Margaropus, Rhipicephalus, Ornithodorus, Otobius, Cheyletidae, for example, Cheyletus, Psorergates, Demodicidae, Trombiculidae, for example, Trombicula, Eutrombicula, Schöngastia, Acomatacurus, Neoschongastia, Euschöngastia, Sarcoptiformes, for example, Notoedres, Sarcoptes, Knemidokoptes, Psoroptidae, for example, Psoroptes, Chorioptes, Otodectes or Tetranychidae, for example, Tetranychus telarius, and Tetranychus urticae.

These mixtures can be employed either by themselves or together with a suitable carrier and/or additive.

Suitable carriers and additives can be solid or liquid and correspond to the substances which are customary in formulation technology, such as, for example, natural or regenerated mineral substances, solvents, diluents, dispersing agents, emulsifiers, wetting agents, adhesives, thickeners, binders or fertilisers.

Such agents can be used in the form of solutions, emulsions, suspensions, granules or dusting agents. The form in which the agents are used depends upon the use to which they are to be put, but fine divisibility of the active substance must be ensured.

The content of active substance in the agents described above is within the range of from 0.1 to 95%. At the same time, it should be mentioned that in the case of application from an aircraft or by means of other suitable application devices, concentrations of up to 99.5% or even pure active substance can be employed.

For the manufacture of solutions it is possible to use solvents, for example, especially alcohols, for example, ethyl or isopropyl alcohol, ketones, for example, acetone or cyclohexanone, aliphatic hydrocarbons, for example, kerosene, and cyclic hydrocarbons, for example, benzene, toluene, xylene, tetrahydronaphthalene and alkylated naphthalenes, also chlorinated hydrocarbons, for example, tetrachlorethane or ethylene chloride and finally also mineral and vegetable oils or mixtures of the above-mentioned substances.

The aqueous forms of preparation are preferably emulsions and dispersions. The compounds of formula (I) and the active substance, either as such or in one of the above-mentioned solvents, are homogenised in water, preferably by means of a wetting agent or dispersing agent. Quaternary ammonia compounds may be mentioned as examples of cationic emulsifiers or dispersing agents, soaps, aliphatic long-chain sulphuric acid monoesters, aliphaticaromatic sulphonic acids and long-chain alkoxyacetic acids as examples of anionic agents and polyglycol ethers of fatty alcohols or ethylene oxide condensation products with p-tert.alkylphenols as non-ionic agents. Concentrates consisting of the active substance, synergistic agent, emulsifier or dispersing agent and, optionally a solvent can also be manufactured. Such concentrates can be diluted before use, for example with water.

Dusting agents may be manufactured by mixing or conjoint grinding of the active substance and the synergistic agent with a solid carrier. Possible carriers are, for example: talc, diatomaceous earth, kaolin, bentonite, calcium carbonate, boric acid and tricalcium phosphate, but also wood flour, cork powder, charcoal and other materials of vegetable origin. Dusting agents may also be prepared by absorbing the substances on a carrier by means of a volatile solvent. Pulverulent preparations and pastes can be rendered capable of suspension in water, and usable as spraying agents, by adding wetting agents and protective colloids.

In many cases the use of granules for the uniform release of the active substance-synergistic agent combinations over a longer period of time is of advantage. These granules can be manufactured by dissolving the active substance in an organic solvent, absorption of this solution by a granular material, for example attapulgite or $SiO_2$, and removal of the solvent. They can also be manufactured by mixing the active substances of formula (I) with polymerisable compounds, after which a polymerisation is carried out which leaves the active substances unaffected, with granulation being effected whilst the polymerisation is still proceeding.

The following Examples illustrate the invention:-

EXAMPLE 1

Dusting agents

Equal parts of a mixture of active substance and synergistic agent and precipitated silica are finely ground. Dusting agents, preferably containing 1 to 6% of active substance, can be manufactured therefrom by mixing with kaolin or talc.

Spraying powders

In order to manufacture a spraying powder, the following components are, for example, mixed and finely ground:

| | |
|---|---|
| 50 | parts of a mixture of active substance and synergistic agent |
| 20 | parts of highly adsorbent silica |
| 25 | parts of bolus alba (kaolin) |
| 1.5 | parts of sodium 1-benzyl-2-stearyl-benzimidazole-6,3'-disulphonate and |
| 3.5 | parts of a reaction product of p-tert. octylphenol and ethylene oxide. |

Emulsion concentrate

The easily soluble mixture of active substance and synergistic agent can also be formulated as an emulsion concentrate in accordance with the following instruction:

| | |
|---|---|
| 20 | parts of active substance and synergistic agent |
| 70 | parts of xylene and |
| 10 | parts of a mixture of a reaction product of an alkylphenol with ethylene oxide and calcium dodecylbenzenesulphonate | are mixed. On dilution to the desired concentration with water, a sprayable emulsion is produced.

Granules 7.5 g of a mixture of active substance and synergistic agent are dissolved in 100 ml of acetone and the acetone solution thus obtained is added to 92 g of granular attapulgite. The whole is well mixed and the solvent is stripped off in a rotary evaporator. Granules containing 7.5% of active substance are obtained.

EXAMPLE 2

Test for synergistic action

Female houseflies, 2 to 5 days' old, were used for this test. Before the start of the experiment the animals were sorted under $CO_2$-narcosis according to sex and the females were gathered in groups of 10. The animals, which were kept motionless with $CO_2$, were treated with a dispenser which under head pressure releases one microliter of the test substance dissolved in acetone. After the treatment the animals were introduced in groups of 10 into Petri dishes into which a cottonwool pad soaked in honey water had been introduced for feeding purposes. After 24 hours the experiment was evaluated by counting the flies which could no longer move. The results quoted in the Table represent average values of the precentage mortality from four repeat experiments.

Per fly [weight of one fly, 20 mg (average value)] the following were employed once for the test:

a) 0.08γ or 0.04γ or 0.02γ of one of the compounds No.

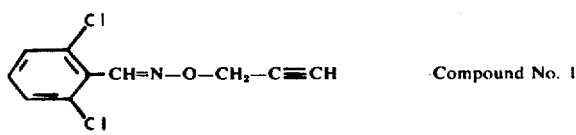 Compound No. 1

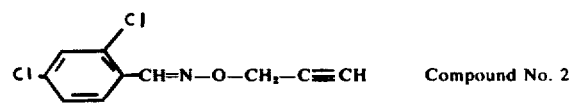 Compound No. 2

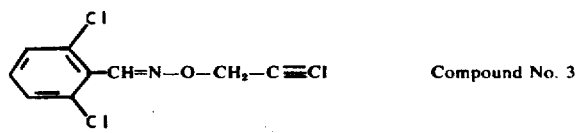 Compound No. 3

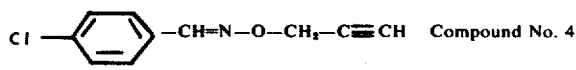 Compound No. 4

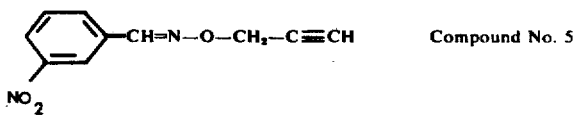 Compound No. 5

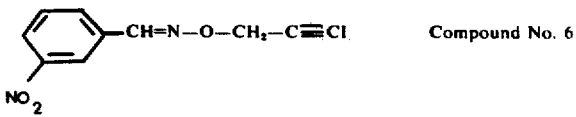 Compound No. 6

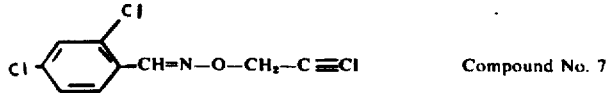 Compound No. 7

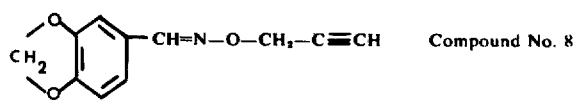 Compound No. 8

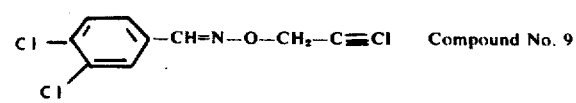 Compound No. 9

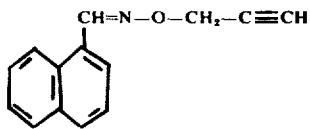 Compound No. 10

Experiment I: Insecticide

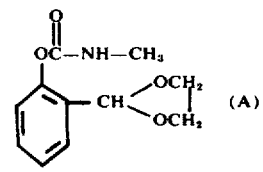 (A)

b. 0.08γ or 0.04γ or 0.02γ of one of the compounds of formulae

+ synergistic agents Nos. 1 to 10

|  | 0.08γ Synergistic Agent | 0.08γ (A) | 0.08γ (A) + 0.08γ Synergistic Agent |
| --- | --- | --- | --- |
| No. 1 | 2.5 ± 2.5 | 14 ± 8.5 | 90 ± 10 |
| No. 2 | 0 | '' | 75 ± 15 |
| No. 3 | 1 | '' | 75 ± 24.5 |
| No. 4 | 0 | '' | 67 ± 19.5 |
| No. 5 | 2.5 ± 2.5 | '' | 63 ± 10 |
| No. 6 | 2.5 ± 2.5 | '' | 61 ± 27 |
| No. 7 | 5 ± 5 | '' | 61 ± 17 |
| No. 8 | 6 ± 5 | '' | 61 ± 19.5 |
| No. 9 | 2.5 ± 2.5 | '' | 37 ± 17 |
| No. 10 | 4 ± 2.5 | '' | 28 ± 24 |

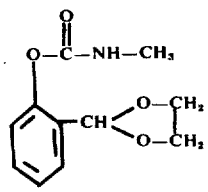 (A)

Insecticide (A) may be prepared by methods taught in British Pat. No. 1,122,663, filed Oct. 4, 1965, and published on Aug. 7, 1968.

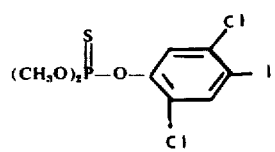 (B)

Experiment II: Insecticide

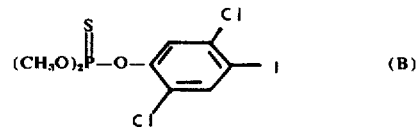 (B)

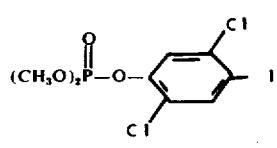 (C)

+ synergistic agents Nos. 1 to 10

|  | 0.04γ Synergistic Agent | 0.04γ (B) | 0.04γ (B) + 0.04γ Synergistic Agent |
| --- | --- | --- | --- |
| No. 1 | 4 ± 4 | 11.2 ± 2.5 | 51 ± 12.5 |
| No. 2 | 0 | '' | 32 ± 22.5 |
| No. 3 | 4 ± 4 | '' | 27 ± 15 |
| No. 4 | 5 ± 5 | '' | 23 ± 10 |
| No. 5 | 0 | '' | 27 ± 7.5 |
| No. 6 | 1 ± 1 | '' | 33 ± 15 |
| No. 7 | 4 ± 4 | '' | 28 ± 20 |
| No. 8 | 0 | '' | 17 ± 15 |
| No. 9 | 6 ± 6 | '' | 32 ± 25 |
| No. 10 | 2.5 ± 2.5 | '' | 18 ± 15 |

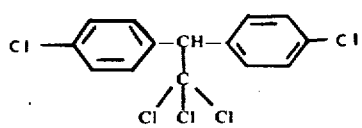 (D)

c. 0.08γ or 0.04γ or 0.02γ of one of the compounds (A), (B), (C) or (D) and 0.08γ or 0.04γ or 0.02γ of one of the compounds Nos. 1 to 10.

Experiment III: Insecticide

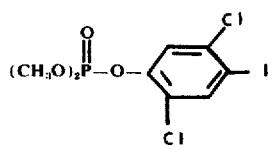 (C)

+ synergistic agents Nos. 1 to 10

|  | 0.04γ Synergistic Agent | 0.04γ (C) | 0.04γ (C) + 0.04γ Synergistic Agent |
|---|---|---|---|
| No. 1 | 2.5 ± 2.5 | 13 ±6.5 | 56 ± 15 |
| No. 2 | " | " | 25 ± 15 |
| No. 3 | " | " | 45 ± 12.5 |
| No. 4 | " | " | 13 ± 10 |
| No. 5 | 7.5 ± 7.5 | " | 40 ± 17.5 |
| No. 6 | 1 ± 1 | " | 31 ± 15 |
| No. 7 | " | " | 33 ± 22.5 |
| No. 8 | 2.5 ± 2.5 | " | 20 ± 17.5 |
| No. 9 | 4 ± 4 | " | 21 ± 17.5 |
| No. 10 | 0 | " | 18 ± 10 |

Experiment IV: Insecticide

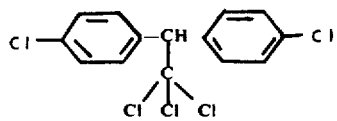 (D)

+ synergistic agents Nos. 1 to 10

|  | 0.02γ Synergistic Agent | 0.02γ (D) | 0.02γ (D) + 0.02γ Synergistic Agent |
|---|---|---|---|
| No. 1 | 0 | 19 ± 12.5 | 71 ± 22.5 |
| No. 2 | 0 | " | 38 ± 15 |
| No. 3 | 1 ± 1 | " | 65 ± 20 |
| No. 4 | 4 ± 4 | " | 28 ± 22.5 |
| No. 5 | 2.5 ± 2.5 | " | 42 ± 17.5 |
| No. 6 | 0 | " | 31 ± 17.5 |
| No. 7 | 1 ± 1 | " | 32 ± 15 |
| No. 8 | 2.5 ± 2.5 | " | 33 ± 10 |
| No. 9 | 4 ± 4 | " | 25 ± 10 |
| No. 10 | 5 ± 5 | " | 20 ± 10 |

EXAMPLE 3

The compound of formula

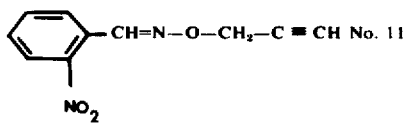 No. 11 was tested as to the influence on the ingestion-contact action of active substances of formulae

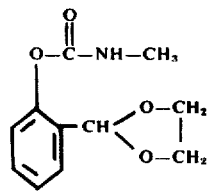 (A)

and

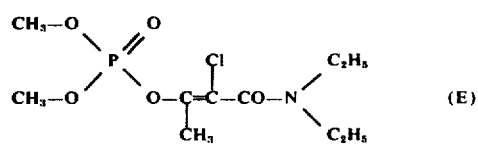 (E)

using Epilachna varivestis. Here the following results were obtained.

Ingestion-contact action in % in the case of Epilachna varivestis

|  | Concentration ppm | after 2 days | 5 days |
|---|---|---|---|
| Compound 11 + Active Substance (A) | 400 + 400 | 100 | 100 |
|  | 200 + 200 | 80 | 100 |
|  | 100 + 100 | 60 | 100 |
|  | 50 + 50 | 60 | 100 |
| Compound 11 + Active Substance (E) | 400 + 400 | 60 | 100 |
|  | 200 + 200 | 60 | 100 |
|  | 100 + 100 | 60 | 100 |
|  | 50 + 50 | 60 | 100 |
| Active Substance (A) | 800 | 80 | 100 |
|  | 400 | 60 | 100 |
|  | 200 | 60 | 80 |
|  | 100 | 0 | 80 |
| Active Substance (E) | 800 | 60 | 80 |
|  | 400 | 0 | 80 |
|  | 200 | 0 | 0 |
|  | 100 | 0 | 0 |

We claim:
1. An insecticidal and acaricidal composition which comprises substantially equal amounts of (1) the oxime ether of the formula:

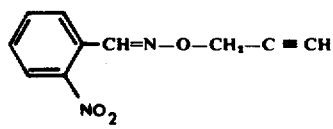

and (2) the carbamic acid derivative of the formula:

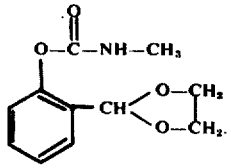

* * * * *